United States Patent [19]

Bailey

[11] 4,107,313

[45] Aug. 15, 1978

[54] α,α-BIS-[4-(R-AMINO)-1-PYRIDINIUM]XY-LENES AND ANTIBACTERIAL AND ANTIFUNGAL USES

[75] Inventor: Denis M. Bailey, East Greenbush, N.Y.

[73] Assignee: Sterling Drug Inc., New York, N.Y.

[21] Appl. No.: 734,729

[22] Filed: Oct. 22, 1976

Related U.S. Application Data

[63] Continuation-in-part of Ser. No. 661,128, Feb. 25, 1976, abandoned.

[51] Int. Cl.$^2$ .................... A01N 9/22; C07D 213/74
[52] U.S. Cl. .................................. 424/263; 252/106; 260/296 D
[58] Field of Search ................ 260/296 D; 424/263; 252/106

[56] References Cited

U.S. PATENT DOCUMENTS 3,516,782   6/1970   Sello et al. ........................... 8/127.6

OTHER PUBLICATIONS

Walker et al., J. Org. Chem., vol. 26, pp. 2740 to 2747 (1961).
Austin et al., J. Pharm. Pharmacol. vol. 11, pp. 80 to 93 (1959).

*Primary Examiner*—Richard L. Raymond
*Attorney, Agent, or Firm*—Paul E. Dupont; B. Woodrow Wyatt

[57] ABSTRACT

α,α'-Bis-[4-(R-amino)-1-pyridinium]xylenes are prepared by reacting a 4-(R-amino)pyridine with an appropriate α,α'-disubstituted xylene. The compounds are useful as antibacterial and antifungal agents.

18 Claims, No Drawings

α,α-BIS-[4-(R-AMINO)-1-PYRIDINIUM]XYLENES AND ANTIBACTERIAL AND ANTIFUNGAL USES

CROSS-REFERENCE TO RELATED APPLICATIONS

This application is a continuation-in-part of prior copending application Ser. No. 661,128, filed Feb. 25, 1976 and now abandoned.

BACKGROUND OF THE INVENTION

1. Field of the Invention

The present invention relates to compositions of matter classified in the art of chemistry as α,α'-bis-[4-(R-amino)-1-pyridinium]xylenes, to a process for the preparation thereof, to compositions containing these compounds and to methods of using the same for controlling bacteria and fungi.

2. Prior Art

Walker U.S. Pat. No. 3,055,902, issued Sept. 25, 1962 discloses a group of bis-(4-amino-1-pyridinium)alkanes as intermediates in the preparation of the corresponding bis-(4-amino-1-piperidino)alkanes stated to have bacteriostatic and bactericidal effects.

G. N. Walker et al., J. Org. Chem. 26, 2740-7 (1961) disclose essentially the subject matter disclosed in the above-noted Walker U.S. patent.

W. C. Austin et al., J. Pharm. Pharmacol. 11, 80-93 (1959) disclose 1,10-bis-(4-amino-1-pyridinium)decane diiodide and 1,10-bis-(4-acetamido-1-pyridinium)decane diiodide. It is stated that certain species among the large, deverse group of quaternary ammonium compounds disclosed possess amebicidal, antibacterial, antifilarial and trypanocidal activity, but no biological data are given for either of the above-named compounds.

Sello U.S. Pat. No. 3,516,782, issued June 23, 1970 discloses 1,1'-(p-phenylenedimethylene)bis(pyridinium chloride) as an agent for imparting crease retention to wool fabrics.

SUMMARY OF THE INVENTION

In a composition aspect, this invention relates to a group of α,α'-bis-[4-(R-amino)-1-pyridinium]xylenes which are useful as antibacterial and antifungal agents.

In other composition aspects the present invention provides antibacterial and antifungal compositions suitable as skin-cleansing agents or for topical application to skin or other living tissues or to inanimate surfaces, which compositions comprise an antibacterially and antifungally effective amount of an α,α'-bis-[4-(R-amino)-1-pyridinium]xylene in combination with a compatible vehicle.

In a method aspect, the present invention provides a method for controlling bacteria and fungi which comprises contacting said bacteria and fungi with an antibacterially and antifungally effective amount of an α,α'-bis-[4-(R-amino)-1-pyridinium]xylene.

In a process aspect this invention relates to a process for preparing α,α'-bis-[4-(R-amino)-1-pyridinium]xylenes which comprises reacting a 4-(R-amino)pyridine with an appropriate α,α'-disubstituted xylene.

DETAILED DESCRIPTION INCLUSIVE OF THE PREFERRED EMBODIMENTS

The invention sought to be patented resides in one of its composition aspects in the α,α'-bis-[4-(R-amino)-1-pyridinium]xylenes having Formula I hereinbelow:

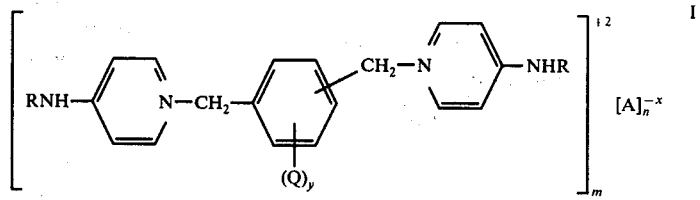

wherein:
R is hydrogen, a straight or branched-chain alkyl group containing from 1 to 18 carbon atoms, or benzyl;
Q is methyl or chlorine;
$y$ is an interger 0 to 4;
A is an anion;
$m$ is 1 or 3;
$n$ is 1 or 2; and,
$x$ is 1, 2 or 3; and,
wherein $(m)\,(2) = (n)\,(x)$.

These compounds are useful as antibacterial and antifungal agents.

Included in the above group are the compounds having Formula I wherein R, A, $m$, $n$ and $x$ have the above-given meaning and wherein:
(a) Q is methyl and $y$ is 0 to 4;
(b) Q is chlorine and $y$ is 1 to 4.

In a further composition aspect the invention sought to be patented resides in an antibacterial and antifungal composition suitable for topical administration which comprises an effective amount of a compound having the Formula I hereinabove and a pharmaceutically acceptable carrier.

In another composition aspect the invention sought to be patented resides in a skin-cleansing composition comprising an antibacterially and antifungally effective amount of a compound having the Formula I hereinabove, a compatible pharmaceutically acceptable surfactant and a compatible pharmaceutically acceptable diluent or carrier.

In yet another composition aspect the invention sought to be patented resides in an antibacterial and antifungal composition suitable for application to inanimate surfaces comprising an antibacterially and antifungally effective amount of a compound having the Formula I hereinabove in combination with a compatible vehicle.

In its method aspect the invention sought to be patented resides in the method for controlling bacteria and fungi on human skin or other tissues or inanimate surfaces which comprises contacting said bacteria and fungi with an antibacterially and antifungally effective amount of a compound having Formula I hereinabove.

The invention sought to be patented resides in its process aspect in the chemical process which comprises reacting a 4-(R-amino)pyridine having the Formula II:

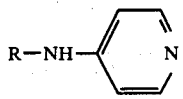

wherein R has the above-given meaning with a disubstituted xylene having the Formula III:

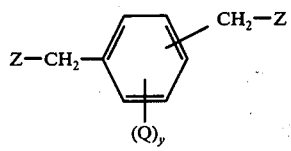

Wherein Q and y have the above-given meanings; and, Z is selected from the group consisting of chloro, bromo, iodo, methanesulfonyloxy, ethanesulfonyloxy, benzenesulfonyloxy, and p-toluenesulfonyloxy.

In the formulas herein R is a straight- or branched-chain alkyl group containing from 1 to 18, preferably from 6 to 12 carbon atoms, for example: methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, isopropyl, 1-methylpropyl, isobutyl, tert-butyl, isopentyl, neopentyl, 1-methylpentyl, 2,2-dimethylbutyl, 2-methylhexyl, 1,4-dimethylpentyl, 2-ethylpentyl, 3-ethylpentyl, 2-methylheptyl, 1-ethylhexyl, 2-ethylhexyl, 2-propylpentyl, 2-methyl-3-ethylpentyl, 3ethylheptyl, 1,3,5-trimethylhexyl, 1,5-dimethyl-4-ethylhexyl, 2-propylheptyl, 5-methyl-2-butylhexyl, 2-propylnonyl, 2-butyloctyl, 1,1-dimethylundecyl, 2-pentylnonyl, 1,2-dimethyltetradecyl, 1,1-dimethylpentadecyl and the like.

When A in the formulas herein is an anion there are included anions of both inorganic and organic acids, for example: bromide, chloride, fluoride, iodide, sulfate, phosphate, nitrate, sulfamate, methanesulfonate, ethanesulfonate, benzenesulfonate, p-toluenesulfonate, naphthalenesulfonate, naphthalenedisulfonate, cyclohexylsulfamate, and the like. Bromide and chloride are preferred.

The compounds of Formula I hereinabove are obtained by reacting a 4-(R-amino)pyridine having Formula II hereinbelow

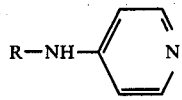

with an α,α'-disubstituted xylene having Formula III hereinbelow

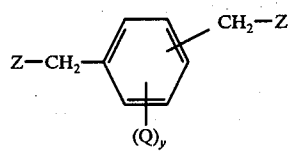

wherein in Formulas II and III R, Q, y and Z have the previously given meanings.

The reaction is conveniently carried out by reacting two moles of a 4-(R-amino)pyridine (Formula II) with one mole of an appropriately α,α'-disubstituted xylene (Formula III) in an inert solvent such as a lower alkanol, acetonitrile, N,N-dimethylformamide, N,N-dimethylacetamide, benzene, toluene, xylene and the like, at a temperature of from about 80° to 150° C. for a period of from 1 to 24 hours. Usually the reactants are heated at 60° to 100° C. in acetonitrile or a lower alkanol for about 2 to 20 hours.

Alternatively, the reaction may be carried out in the absence of a solvent by heating stoichiometric quantities of the reactants at temperatures up to 120°-150° C. for about 2 to 5 hours.

The resulting α,α'-bis-[4-(R-amino)-1-pyridinium]xylenes (Formula I) are isolated according to conventional methods, for example by filtration, if the product is insoluble in the reaction medium, or by dilution of the reaction mixture with a non-polar solvent such as ether, benzene or hexane in order to precipitate the product or by evaporation of the reaction medium to leave the product as a residue. The isolated crude product can be purified by crystallization from a suitable solvent in the presence of an adsorbent, e.g., charcoal or diatomaceous earth.

The α,α'-bis-[4-(R-amino)-1-pyridinium]xylenes produced in accordance with the above-described method will, of course, contain an anion (A in Formula I) which corresponds to the leaving group of the reactant α,α'-disubstituted xylene (Z in Formula III).

However, the anionic moiety of these compounds can be varied, if desired, according to conventional ion exchange methods, for example by passing a solution of a pyridinium compound in a suitable solvent, e.g., methanol, ethanol or water through a bed of synthetic ion exchange resin containing the desired anion. The solvent is evaporated and the resulting pyridinium compound containing the desired anion is purified by recrystallization from a suitable solvent.

Thus, should the anionic portion of a given compound accord to that species characteristics such as solubility, stability, molecular weight, physical appearance, toxicity or the like, which render that form of the compound unsuitable for a desired purpose, it can readily be converted to another, more suitable form. For use on the skin or other tissues pharmaceutically acceptable anions such as fluoride, chloride, bromide, iodide, methanesulfonate, and the like, are of course employed.

The 4-(R-amino)pyridines (Formula II) which are used as starting materials generally are known or, if specifically new, are prepared according to the precedures described for preparation of the known compounds.

Conveniently, the 4-(R-amino)pyridines are prepared by reacting 4-chloro or 4-bromopyridine or N-(4-pyridyl)pyridinium chloride hydrochloride with an appropriately substituted amine. The reaction is usually carried out by heating the reactants in the absence of a solvent at 150°-225° C. for about 1½ to 3 hours. The product is isolated in a conventional manner, for example by extraction from alkaline aqueous medium into an organic solvent such as ether, methylene chloride or chloroform, evaporation of the organic solvent and crystallization of the residue from an appropriate solvent.

Alternatively, the 4-(R-amino)pyridines are obtained by catalytic hydrogenation of a mixture containing 4-aminopyridine and a carbonyl compound containing the appropriate carbon content. The reaction is usually carried out at a temperature of 50°–70° C. in a suitable solvent, for example ethanol, under a hydrogen pressure of 20–60 psi, in the presence of a palladium hydrogenation catalyst. A hydrogenation time of 4–10 hours is generally satisfactory. The use of a large excess of the carbonyl compound, i.e., 200% or greater advantageously results in high yields of pure product in a reaction time of 5 hours or less. Following removal of the catalyst the product is isolated by evaporation of the solvent and either distilling the residue or crystallizing the latter from a suitable solvent.

Reaction of an aldehyde having the appropriate carbon content with 4-aminopyridine in the presence of formic acid at elevated temperatures also provides the 4-(R-amino)pyridines.

The 4-(R-amino)pyridines can also be obtained by acylation of 4-aminopyridine with an acyl halide having the appropriate carbon content followed by reduction of the resulting amide. The acylation is carried out according to art-recognized methods, for example by reacting 4-aminopyridine with an acyl halide in an inert solvent such as methylene dichloride or chloroform in the presence of an acid acceptor such as triethylamine. The amide so-produced is then reduced with a complex metal hydride such as lithium aluminum hydride in a suitable solvent such as tetrahydrofuran, ether or dioxane and the amine product isolated in accordance with known procedures.

The $\alpha,\alpha'$-disubstituted xylenes having Formula III also used as starting materials generally are known compounds, or if specifically new can be prepared according to the procedures used for preparing the known compounds.

Thus an appropriate chloro or methyl-substituted phthalic, isophthalic or terephthalic acid or ester is reduced to the corresponding xylene-$\alpha,\alpha'$-diol with a metal hydride such as lithium aluminum hydride in a suitable solvent such as tetrahydrofuran, ether or dioxane. The xylene-$\alpha,\alpha'$-diol so-produced is then converted to an $\alpha,\alpha'$-dihaloxylene, for example by reaction with hydrogen bromide, phosphorous tribromide, phosphorus oxychloride, thionyl chloride or potassium iodide and orthophosphoric acid according to art-recognized methods. Alternatively, the xylene-$\alpha,\alpha'$-diol can be converted to a sulfonate ester by reaction with methane-, ethane-, benzene- or p-toluenesulfonyl chloride in the presence of an acid acceptor such as pyridine in accordance with well known procedures.

As described more fully hereinbelow the compounds having Formula I have in vitro antimicrobial activity against several species of microorganisms among which are included both gram positive and gram negative bacteria and several species of fungi. The compounds are therefore indicated for use as antimicrobial or antiseptic agents which can be applied topically to effect the degerming of human skin and other tissues and to sanitize and disinfect inanimate surfaces. Thus, the compounds can be used in topical antiseptic solutions for the treatment of wounds, in antibacterial cleansing agents such as surgical hand scrubs, patient pre-operative skin preparations, soaps and shampoos, or in household and industrial cleaners and disinfectants. The compounds are adapted for the above indicated utilities by combining them with conventional diluents or carriers, surfactants, buffering agents, perfumes and coloring agents, and are applied to a surface to be disinfected by conventional methods such as scrubbing, spraying, swabbing, immersion and the like.

For use as skin-cleansing agents the bis-[4-(R-amino)-1-pyridinium]xylenes can be prepared as liquids, or, if desired, the liquid formulations can be thickened by certain additives into a gel or paste or molded into a bar according to methods known in the art. For example, the compounds can be formulated with pharmaceutically acceptable non-ionic surfactants such as the polyoxyethylene polyoxypropylene copolymers described in U.S. Pat. No. 3,855,140, amine oxides such as stearyl dimethyl amine oxide described in U.S. Pat. No. 3,296,145 and the like or with mixtures of these. The formulations may additionally contain pharmaceutically acceptable diluents such as water, lower alkanols and the like, acids, bases, or buffering agents so as to maintain a pH of 5.0 to 7.5, and optionally, perfumes and coloring agents. The bis-[4-(R-amino)-1-pyridinium]xylene component of such formulations is generally present in a concentration of approximately 0.5 to 2.0 percent by weight, preferably 1.0 percent by weight.

When prepared as a tincture the $\alpha,\alpha'$-bis-[4-(R-amino)-1-pyridinium]xylenes may be formulated with water, a lower alkanone, e.g., acetone, and a lower alkanol such as ethanol. If desired the tincture may be tinted with a coloring agent. The active ingredient is generally present in a concentration of about 0.05 to 1.0 percent (w/v) preferably 0.1 percent (w/v).

Alternatively, the compounds can be formulated in suitable pharmaceutical vehicles for treating bacterial and fungal infections for example as lotions, ointments or creams by incorporating them in conventional lotion, ointment or cream bases, for example, alkyl polyether alcohols, cetyl alcohol, stearyl alcohol and the like, or as powders by incorporating them in conventional powder bases such as starch, talc and the like, or as jellies, by incorporating them in conventional jelly bases such as gycerol and tragacanth. They can also be formulated for use as aerosol sprays or foams.

When used for sanitizing and disinfecting inanimate surfaces the compounds can be formulated with known detergents and builders such as trisodium phosphate, borax and the like. The $\alpha,\alpha'$-bis-[4-(R-amino)-1-pyridinium]xylene component of such formulations is generally present in a concentration up to about 10 percent by weight.

It will, of course, be appreciated that the vehicles, diluents, carriers and additives contained in the above-described formulations are compatible with the active ingredient, i.e., the antibacterial and antifungal effectiveness of the $\alpha,\alpha'$-bis-[4-(R-amino)-1-pyridinium]xylenes is not vitiated by effects ascribable to the nature of the vehicle, diluent, carrier or other additive.

The molecular structures of the compounds of the invention were assigned on the basis of study of their infrared and NMR spectra, and confirmed by the correspondence between calculated and found values for elemental analyses for the elements.

The invention is illustrated by the following examples without, however, being limited thereto.

EXAMPLE 1

A. A mixture containing 130 g. (0.67 mole) of 4-bromopyridine hydrochloride and 152 g. (1.0 mole) of n-heptylamine hydrochloride was heated in an oil bath. When the bath temperature reached 180°–185° C. the reaction mixture began to melt and stirring was begun. At 190°–195° C. melting was complete and the liquid mixture was stirred and heated at 210°–220° C. for 2.5 hours. The reaction mixture was then cooled to room temperature and the resulting solid was dissolved in water, made alkaline with 35% aqueous sodium hydroxide and the product extracted with chloroform. The chloroform extracts were dried over anhydrous sodium sulfate and evaporated to dryness under reduced pressure. The resulting viscous oil was diluted with a small amount of n-hexane and cooled to give a solid which was collected by filtration and air-dried to afford 86.6 g. of 4-(heptylamino)pyridine, m.p. 49°–51° C.

B. Alternatively, 4-(heptylamino)pyridine was prepared as follows: A mixture containing 229 g. (1.0 mole) of N-(4-pyridyl)pyridinium chloride hydrochloride and 228 g. (1.5 moles) of n-heptylamine hydrochloride was heated 2 hours with stirring in an oil bath at a bath temperature of 215° C. The reaction mixture was cooled to 80° C., diluted with icewater, made alkaline with 35% aqueous sodium hydroxide and extracted successively with ether and chloroform. The organic extracts were combined and evaporated to dryness under reduced pressure. The residual viscous oil was dissolved in ether and the ethereal solution was washed with water. The aqueous wash was back-extracted with chloroform and the chloroform extracts were combined with the ethereal solution. The combined organic solutions were dried over anhydrous sodium sulfate and evaporated to dryness under reduced pressure. Cooling the residual oil to −78° C. effected partial solidification. The semi-sold was diluted with a small amount of ether and filtered. The solid so-obtained was dissolved in a mixture of acetonitrile and chloroform, the resulting solution treated with decolorizing carbon, filtered, and the filtrate evaporated to dryness under reduced pressure. The resulting semi-solid was diluted with a small amount of ether and cooled. The solid thus-produced was collected by filtration and washed with a small volume of cold ether to give, after drying, 84.6 g. of 4-(heptylamino)pyridine, m.p. 50°–52° C.

C. To a warm, stirred solution containing 11.52 g. (0.06 mole) of 4-(heptylamino)pyridine in 100 of acetonitrile was added in small portions a solution containing 7.92 g. (0.03 mole) of α,α'-dibromo-p-xylene in 150 ml. of acetonitrile. After addition was complete a large mass of colorless crystals had separated from solution. The reaction mixture was heated under reflux 6 hours. After cooling to room temperature the solid product was collected by filtration, washed with acetonitrile-ether, combined with 3.1 g. of product obtained in a previous run and dried 28 hours at 100° C/0.1 mm. to give 22.0 g. of α,α'-bis-[4-(heptylamino)pyridinium]-p-xylene dibromide, m.p. 297°–298° C.

EXAMPLE 2

A. A mixture containing 100.0 g. (0.51 mole) of 4-bromopyridine hydrochloride and 110 g. (0.8 mole) of n-hexylamine hydrochloride was heated in an oil bath. When the bath temperature reached 175°–180° C. the reaction mixture began to melt and stirring was begun. The temperature of the bath was then raised to 227° C. and the stirring continued 3.5 hours. After cooling to room temperature the reaction mixture was dissolved in hot water, the resulting solution cooled with ice, made alkaline with dilute aqueous sodium hydroxide and extracted with chloroform. The chloroform extracts were dried over anhydrous sodium sulfate and evaporated to dryness under reduced pressure. The residue was triturated with ether and cooled. The resulting solid was collected by filtration and washed with cold ether. Evaporation of the filtrate afforded a second crop of solid. The crops were combined, dissolved in chloroform, treated with decolorizing carbon and filtrated. The filtrate was evaporated under reduced pressure, and the residue was triturated with cold ether. The product thus-obtained was collected by filtration, washed with cold ether and dried to give 63.6 g. of 4-(hexylamino)pyridine, m.p. 66°–68° C. Evaporation of the filtrate afforded an additional 7.0 g., m.p. 65°–67° C.

B. Alternatively, 4-(hexylamino)pyridine was prepared as follows: A mixture containing 229 g. (1 mole) of N-(4-pyridyl)pyridinium chloride hydrochloride and 207 g. (1.5 moles) of n-hexylamine hydrochloride was stirred and heated 1.75 hours at 175°–185° C. The reaction was cooled and diluted with 750 ml. of ice-water. The resulting solution was made alkaline with 35% aqueous sodium hydroxide and after further dilution with 1 liter of water was extracted with ether followed by dichloromethane. The organic extracts were combined, dried over anhydrous sodium sulfate and evaporated to dryness under reduced pressure. The residue was crystallized from ether, redissolved in chloroform, the resulting solution treated with decolorizing carbon and filtered. The filtrate was evaporated to dryness under reduced pressure and the residue was triturated with a mixture of ether and acetonitrile. The solid thus-obtained was again dissolved in chloroform and the resulting solution treated with decolorizing carbon and filtered. The filtrate was evaporated to dryness under reduced pressure and the residue was triturated with cold ether to give 71.0 g. of 4-(hexylamino)pyridine, m.p. 68°–70° C.

C. Following a procedure to that described in Example 1C but employing 11.6 g. (0.065 mole) of 4-(hexylamino)pyridine and 8.7 g. (0.033 mole) of α,α'-dibromo-p-xylene and refluxing the reaction mixture 20 hours, there was obtained 19.3 g. of α,α'-bis-[4-(hexylamino)pyridinium]p-xylene dibromide m.p. 313°–315° C.

EXAMPLE 3

A suspension of 19 g. of 4-aminopyridine and 23 g. of α,α'-dichloro-2,3,5,6-tetramethyl-p-xylene in 600 ml. of methanol was heated on a steam bath to effect complete solution. After filtering from a small amount of insoluble material the clear solution was warmed gently on the steam bath for 2 hours during which time a white solid began to separate. The mixture was cooled to room temperature and the solid product was collected by filtration, washed successively with methanol and ether and dried 24 hours under vacuum at 110° C. to give 29 g. α,α'-bis-(4-amino-1-pyridinium)-2,3,5,6-tetramethyl-p-xylene dichloride, m.p. > 340° C.

EXAMPLE 4

To a hot solution containing 12.5 g. (0.132 mole) of 4-aminopyridine in 100 ml. of 2-propanol was added 11.6 g. (0.066 mole) of α,α'-dichloro-p-xylene followed by 400 ml. of methanol. The mixture was heated to effect complete solution. After filtering from a small amount of insoluble material the clear solution was diluted with 500 ml. of ethyl acetate and cooled to room temperature. The solid product was collected by fitration, washed with ethylacetate and dried to give 16 g. of α,α'-bis-(4-amino-1-pyridinium)-p-xylene dichloride, m.p. 332°–335° C.

The following are further illustrative examples of the α,α'-bis-[4-(R-amino)-1-pyridinium]xylenes of Formula I which are obtained in accordance with the above-described procedures:

α,α'-Bis-[4-(ethylamino)-1-pyridinium]-p-xylene dibromide by reacting α,α'-dibromo-p-xylene with 4-(ethylamino)pyridine;

α,α'-Bis-[4-(2-ethylhexylamino)-1-pyridinium]-p-xylene dichloride by reacting α,α'-dichloro-p-xylene with 4-(2-ethylhexylamino)pyridine (b.p. 145°–150° C./0.9 mm.) which was prepared by reacting N-(4-pyridyl)pyridinium chloride hydrochloride with 2-ethylhexylamine hydrochloride;

α,α'-bis-[4-(decylamino)-1-pyridinium]-p-xylene dibromide by reacting α,α'-dibromo-p-xylene with 4-(decylamino)pyridine (m.p. 71°–73° C.) which was prepared by reacting N-(4-pyridyl)pyridinium chloride hydrochloride with n-decylamine hydrochloride;

α,α'-bis-[4-(dodecylamino)-1-pyridinium]-p-xylene dichloride by reacting α,α'-dichloro-p-xylene with 4-(dodecylamino)pyridine;

α,α'-bis-[4-(octadecylamino)-1-pyridinium]-p-xylene dibromide by reacting α,α'-dibromo-p-xylene with 4-(octadecylamino)pyridine which in turn is obtained by reacting N-(4-pyridyl)pyridinium chloride hydrochloride with octadecylamine hydrochloride;

α,α'-bis-[4-(tetradecylamino)-1-pyridinium]-m-xylene dichloride by reacting α,α'-dichloro-m-xylene with 4-(tetradecylamino)pyridine (m.p. 91°–93° C.) which was prepared by reacting N-(4-pyridyl)pyridinium chloride hydrochloride with tetradecylamine hydrochloride;

α,α'-bis-[4-(butylamino)-1-pyridinium]-o-xylene dibromide by reacting α,α'-dibromo-o-xylene with 4-(butylamino)pyridine;

α,α'-bis-[4-(3-ethylheptylamino)-1-pyridinium]-5-methyl-m-xylene didromide by reacting α,α'-dibromo-5-methyl-m-xylene with 4-(3-ethylheptylamino)pyridine which in turn is obtained by reacting N-(4-pyridyl)pyridinium chloride hydrochloride with 3-ethylheptylamine hydrochloride;

α,α'-bis-[4-(2-methylheptylamino)-1-pyridinium]-2,5-dimethyl-p-xylene dibromide by reacting α,α'-dibromo-2,5-dimethyl-p-xylene with 4-(2-methylheptylamino)pyridine which in turn is obtained by reacting N-(4-pyridyl)pyridinium chloride hydrochloride with 2-methylheptylamine hydrochloride;

α,α'-bis[4-(octylamino)-1-pyridinium]-2,4,6-trimethyl-m-xylene dichloride by reacting α,α'-dichloro-2,4,6-trimethyl-m-xylene with 4-(octylamino) pyridine (M.P. 62°–63° C.) which was prepared by reacting N-(4-pyridyl)pyridinium chloride hydrochloride with n-octylamine hydrochloride;

α,α'-bis:[4-(2,2,-dimethylbutylamino)-1-pyridinium]-2-chloro-p-xylene dichloride by reacting α,α',2-trichloro-p-xylene with 4-(2,2-dimethylbutylamino)pyridine which in turn is obtained by reacting N-(4-pyridyl)pyridinium chloride hydrochloride with 2,2-dimethylbutylamine hydrochloride;

α,α'-bis-[4-(methylamino)-1-pyridinium]-4-chloro-o-xylene dibromide by reacting α,α'-dibromo-4-chloro-o-xylene with 4-(methylamino)pyridine;

α,α'-bis-[4-(2-propylepentylamino)-1-pyridinium]-2,5-dichloro-p-xylene dichloride by reacting α,α',2,5-tetrachloro-p-xylene with 4-(2-propylpentylamino)pyridine which in turn is obtained by reacting N-(4-pyridyl)pyridinium chloride hydrochloride with 2-propylpentylamine hydrochloride;

α,α'-bis-[4-(1,1-dimethylundecylamino)-1-pyridinium]-2,3,5-trichloro-p-xylene dichloride by reacting α,α',2,3,5-pentachloro-p-xylene with 4-(1,1-dimethylundecylamino)pyridine which in turn is obtained by reacting N-(4-pryidyl)pyridinium chloride hydrochloride with 1,1-dimethylundecylamine hydrochloride;

α,α'-bis-[4-(nonylamino)-1-pyridinium]-2,3,5,6-tetrachloro-p-xylene dichloride by reacting α,α',2,3,5,6-hexachloro-p-xylene with 4-(nonylamino)pyridine (m.p. 59°–60° C.) which was prepared by reacting N-(4-pyridyl)pyridinium chloride hydrochloride with n-nonylamine hydrocloride;

α, α'-bis-[4-(benzylamino)-1-pyridinium-p-xylene dibromide by reacting α,α'-dibromo-p-xylene with 4-(benzylamino)pyridine which in turn is obtained by reacting N-(4-pyridyl)pyridinium chloride hydrochloride with benzylamine; and, α,α'-bis-[4-(benzylamino)-1-pyridinium]-2-chloro-p-xylene dichloride by reacting α,α',2-trichloro-p-xylene with 4-(benzylamino)pyridine which in turn is obtained by reacting N-(4-pyridyl)pyridinium chloride hydrochloride with benzylamine.

The antibacterial and antifungal activity of illustrative examples of the compounds of Formula I was determined using a modification of the Autotiter method described by Goss et al., Applied Microbiology 16 (9) 1,414–1,416 (1968) in which a 1,000 mcg./ml. solution of the test compound is prepared. To the first cup of the Autotray is added 0.1 ml. of the test solution. Activation of the Autotiter initiates a sequence of operations by which 0.05 ml. of the test compound solution is withdrawn from the cup by a Microtiter transfer loop and diluted in 0.05 ml. of sterile water. Following this operation, 0.05 ml. of inoculated double-strength semisynthetic medium (glucose) is added automatically to each cup. The overall operation results in final drug concentration ranging from 500 to 0.06 mcg./ml. in twofold decrements. The Autotray is incubated for 18–20 hours at 37° C. at which time the trays are examined visually for growth as evidenced by turbidity, and the concentration of the last sample in the series showing no growth (or no turbidity) is recorded as the minimal inhibitory concentration (MIC) in mcg./ml. The compounds were thus tested as solutions against a variety of gram positive and gram negative bacteria including *Staphylococcus aureus, Proteus mirabilis, Escherichia coli, Klebsiella pneumoniae, Pseudomonas aeruginosa, Streptococcus pyogenes,* and against such fungi as *Aspergillus niger, Candida albicans* and *Trichophyton mentagrophytes.*

Numerical, antibacterial and antifungal test data for illustrative examples are presented in Table A hereinbelow. Corresponding data for two known compounds, viz. 1,8-bis-(4-amino-1-pyridinium)octane dibromide (Reference Compound I) and 1,10-bis-(4-amino-1-pyridinium)decane dibromide (Reference Compound II) are also included in Table A for purposes of comparison.

Antibacterial effectiveness in the presence of serum was determined for representative examples by the standard serial tube dilution test wherein paired comparisons of minimum inhibitory concentrations (MIC) were determined in the absence and in the presence of heat inactivated (30 min. at 56° C.) horse serum in the test medium. The presence of 40% serum resulted in an eight-fold increase in the minimum inhibitory concentration [MIC (mcg./ml.)] of the compound of Example 1C vs. both *Staphylococcus aureus* and *Eschericia coli* and a four-fold increase in the minimum inhibitory concen-

| | | | | | In Vitro Antibacterial and Antifungal Activity | | | | | | | |
|---|---|---|---|---|---|---|---|---|---|---|---|---|
| | | | | | MIC (mcg./ml.) | | | | | | | |
| Cpd. of Ex. No. | S. aureus Smith | E. coli Vogel | K. penumo. 39645 | P. mirab. MGH-1 | Ps. aerug. MGH-2 | E. coli AB1932-11 | E. coli 100/B22 | S. pyogen. C203 | A. niger. 16404 | C. albic. 10231 | C. albica. Wisc. | T. menta. 9129 |
| 1C | 1.95 | 15.6 | 125 | 125 | 125 | 7.8 | 15.6 | 3.9 | 125 | 125 | 125 | 125 |
| 2C | 1.44 | 23.2 | 92.6 | 92.6 | 92.6 | 5.8 | 11.6 | 1.0 | 23.2 | 23.2 | 46.3 | 5.8 |
| 3 | 31.3 | 500 | 500 | 500 | 500 | — | — | — | 500 | 500 | — | 250 |
| 4 | 250 | 500 | 500 | 500 | 500 | — | — | — | 31.3 | 500 | — | — |
| I | 31.3 | 125 | >500 | >500 | >500 | 125 | 250 | 31.3 | 125 | 125 | 125 | 125 |
| II | 7.8 | 62.5 | 250 | >500 | 500 | 31.3 | 62.5 | 7.8 | 125 | 62.5 | 62.5 | 15.6 |

I claim:
1. A compound having the formula

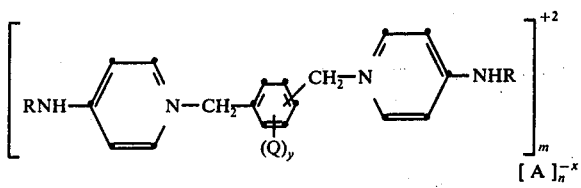

wherein:
R is hydrogen, a straight or branched-chain alkyl group containing from 1 to 18 carbon atoms, or benzyl;
Q is methyl or chlorine;
y is an integer 0 to 4;
A is an anion;
m is 1 or 3;
n is 1 or 2; and
x is 1, 2 or 3; and,
wherein $(m)(2) = (n)(x)$.

2. A compound having the formula

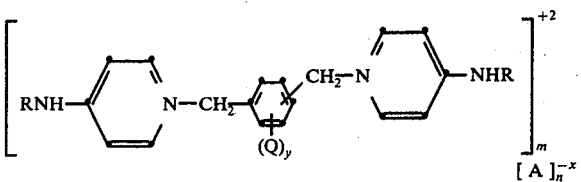

wherein:
R is hydrogen, a straight or branched-chain alkyl group containing from 1 to 18 carbon atoms, or benzyl;
Q is methyl;
y is an integer 0 to 4;
A is an anion;
m is 1 or 3;
n is 1 or 2; and
x is 1, 2 or 3; and,
wherein $(m)(2) = (n)(x)$.

3. A compound according to claim 2 where R is hydrogen.

4. A compound according to claim 2 wherein R is a straight or branched-chain alkyl group containing from 6 to 12 carbon atoms.

5. A compound according to claim 3 wherein the $(Q)_y$-xylylene group linking the 4-(R-amino)-1-pyridinium groups is $(Q)_y$-p-xylylene 6. A compound according to claim 4 wherein the $(Q)_y$-xylylene group linking the 4-(R-amino)-1-pyridinium groups is $(Q)_y$-p-xylylene.

7. A compound having the formula

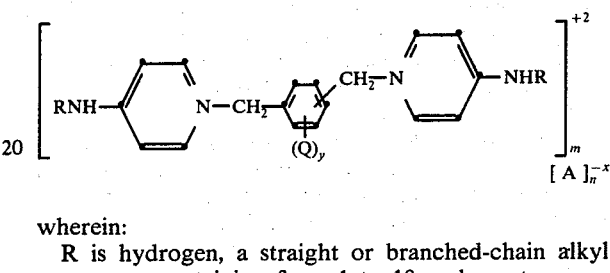

wherein:
R is hydrogen, a straight or branched-chain alkyl group containing from 1 to 18 carbon atoms, or benzyl;
Q is chlorine;
y is an integer 1 to 4;
A is an anion;
m is 1 or 3;
n is 1 or 2; and
x is 1, 2 or 3; and,
wherein $(m)(2) = (n)(x)$.

8. A compound according to claim 7 wherein R is a straight or branched-chain alkyl group containing from 6 to 12 carbon atoms.

9. α,α'-Bis-(4-amino-1-pyridinium)-p-xylene dichloride according to claim 5.

10. α,α'-Bis-(4-amino-1-pyridinium)-2,3,5,6-tetramethyl-p-xylene dichloride according to claim 5.

11. α,α'-Bis-[4-(hexylamino)-1-pyridinium]-p-xylene dibromide according to claim 6.

12. α,α'-Bis-[4-(heptylamino)-1-pyridinium]-p-xylene dibromide according to claim 6.

13. An antibacterial and antifungal composition suitable for topical administration comprising an effective amount of a compound according to claim 1 wherein A is a pharmaceutically acceptable anion, and a pharmaceutically acceptable carrier.

14. A skin-cleansing composition comprising an antibacterially and antifungally effective amount of a compound according to claim 1 wherein A is a pharmaceutically acceptable anion, a compatible pharmaceutically acceptable surfactant and a compatible pharmaceutically acceptable diluent or carrier.

15. A skin-cleansing composition comprising an antibacterially and antifungally effective amount of a compound according to claim 6 wherein A is a pharmaceutically acceptable anion, a compatible pharmaceutically acceptable surfactant and a compatible pharmaceutically acceptable diluent 16. An antibacterial and antifungal composition suitable for application to inanimate surfaces comprising an effective amount of a compound according to claim 1 in combination with a compatible vehicle.

17. A method for controlling bacteria and fungi on human skin or other tissues or inanimate surfaces which comprises contacting said bacteria and fungi with an antibacterially and antifungally effective amount of a compound according to claim 1 wherein A is a pharaceutically acceptable anion when said compound is applied to human skin or other tissues.

18. A method for controlling bacteria and fungi on human skin or other tissue or inanimate surfaces which comprises contacting said bacteria and fungi with an antibacterially and antifungally effective amount of a compound according to claim 6 wherein A is a pharmaceutically acceptable anion when said compound is applied to human skin or other tissues.

* * * * *

UNITED STATES PATENT AND TRADEMARK OFFICE
CERTIFICATE OF CORRECTION

PATENT NO. : 4,107,313
DATED : August 15, 1978
INVENTOR(S) : Denis M. Bailey

It is certified that error appears in the above-identified patent and that said Letters Patent are hereby corrected as shown below:

Column 1, line 41, "deverse" should read -- diverse --.

Column 3, line 32, "3ethylheptyl" should read -- 3-ethylheptyl --

Column 4, lines 50-51, "precedures" should read -- procedures--

Column 4, line 66, "hydrogeneration" should read -- hydrogenation --.

Column 12, Claim 15, line 61, -- or carrier. -- should be added after -- diluent --.

Column 13, Claim 18, line 6, "tissue" should read --tissues--.

Signed and Sealed this

Thirteenth Day of November 1979

[SEAL]

Attest:

RUTH C. MASON
*Attesting Officer*

LUTRELLE F. PARKER
*Acting Commissioner of Patents and Trademarks*